United States Patent
Murayama

(10) Patent No.: US 8,118,734 B2
(45) Date of Patent: Feb. 21, 2012

(54) ENDOSCOPE ILLUMINATION OPTICAL SYSTEM

(75) Inventor: Minoru Murayama, Tokyo (JP)

(73) Assignee: Hoya Corporation, Tokyo (JP)

( * ) Notice: Subject to any disclaimer, the term of this patent is extended or adjusted under 35 U.S.C. 154(b) by 1217 days.

(21) Appl. No.: 11/843,241

(22) Filed: Aug. 22, 2007

(65) Prior Publication Data
US 2008/0051636 A1    Feb. 28, 2008

(30) Foreign Application Priority Data
Aug. 25, 2006  (JP) .................. 2006-229645

(51) Int. Cl.
*A61B 1/06*       (2006.01)
*G02B 9/06*       (2006.01)

(52) U.S. Cl. ......... 600/177; 600/176; 359/794; 359/809

(58) Field of Classification Search .............. 600/176, 600/177, 178; 359/707, 794, 809; 385/33
See application file for complete search history.

(56) References Cited

U.S. PATENT DOCUMENTS

| | | | |
|---|---|---|---|
| 4,415,240 A | | 11/1983 | Nishioka et al. |
| 4,580,552 A | * | 4/1986 | Nishioka et al. .............. 600/177 |
| 4,610,513 A | * | 9/1986 | Nishioka et al. ............... 385/33 |
| 4,929,070 A | * | 5/1990 | Yokota et al. .................. 600/177 |
| 5,485,316 A | * | 1/1996 | Mori et al. ..................... 359/708 |
| 5,951,464 A | * | 9/1999 | Takahashi et al. ............. 600/176 |
| 5,980,454 A | * | 11/1999 | Broome ........................ 600/176 |
| 6,582,363 B2 | | 6/2003 | Adachi et al. |
| 7,585,274 B2 | * | 9/2009 | Homma .......................... 600/160 |
| 2001/0003142 A1 | * | 6/2001 | Koshikawa .................... 600/177 |

FOREIGN PATENT DOCUMENTS

| | | |
|---|---|---|
| JP | 56-020428 | 2/1981 |
| JP | 2-140519 | 11/1990 |
| JP | 5-119272 | 5/1993 |
| JP | 5-157967 | 6/1993 |
| JP | 8-320440 | 12/1996 |
| JP | 2000-275547 | 10/2000 |
| JP | 2002-182126 | 6/2002 |
| JP | 2005-345787 | 12/2005 |

* cited by examiner

*Primary Examiner* — John P Leubecker
(74) *Attorney, Agent, or Firm* — Greenblum & Bernstein, P.L.C.

(57) ABSTRACT

An endoscope illumination optical system includes a surface light source, a positive first lens element, a positive second lens element, in this order from the surface light source.
The endoscope illumination optical system satisfies the following conditions:

$$0.40 < f/D < 0.53 \quad (1)$$

$$0.40 < 0.5 \cdot D \cdot \theta < 0.56 \quad (2)$$

wherein
f: the combined focal length of the positive first lens element and the positive second lens element;
D: the maximum diameter of the surface light source;
R1: the radius of curvature of a first surface, of the positive first lens element, facing toward the surface light source;
R2: the radius of curvature of a second surface, of the positive first lens element, facing toward a surface to be illuminated;
n1: the refractive index of the positive first lens element;
d1: the thickness of the positive first lens element; and
θ designates an angle defined as (1+0.85d1/R2)(1−1/n1)/R1−1.05/R2.

10 Claims, 9 Drawing Sheets

ENDOSCOPE ILLUMINATION OPTICAL SYSTEM

BACKGROUND OF THE INVENTION

1. Field of the Invention

The present invention relates to an endoscope illumination optical system.

2. Description of the Prior Art

Conventionally, endoscope illumination optical systems have been constituted by a light guide (surface light source) and a planoconcave lens element provided at an exit end of the light guide.

However, the planoconcave lens element cannot evenly distribute the light transmitted from the light guide, and the amount of illumination is not sufficient.

Endoscope illumination optical systems which include two positive lens elements are disclosed in, e.g., Japanese Unexamined Patent Publication (JUPP) No. S56-20428, JUPP No. H08-320440, JUPP No. 2000-275547, JUPP No. 2005-345787, and Japanese Unexamined Utility Model Publication No. H02-140519.

However, similar to the planoconcave lens element, the two positive lens elements cannot evenly distribute the light. Specifically, the periphery of a surface to be illuminated cannot suitably be illuminated. Namely, the light-utilization efficiency of an endoscope illumination optical system is insufficient.

Furthermore, JUPP No. 2002-182126 discloses an illumination optical system employing three positive lens elements; and JUPP No. H05-119272 and JUPP No. H05-157967 disclose an illumination optical system employing an aspherical surface. However, the production costs of these illumination optical systems are high.

SUMMARY OF THE INVENTION

The present invention is to provide an endoscope illumination optical system with two positive lens elements, which has the following features:

(i) a superior light-distribution characteristic by which the periphery of an area to be illuminated is suitably illuminated;
(ii) a high light-utilization efficiency; and
(iii) low production costs.

According to an aspect of the present invention, there is provided an endoscope illumination optical system including a surface light source, a first lens element having a positive refractive power (hereinafter, a positive first lens element), and a second lens element having a positive refractive power (hereinafter, a positive second lens element), in this order from the surface light source.

The endoscope illumination optical system satisfies the following conditions:

$$0.40 < f/D < 0.53 \tag{1}$$

$$0.40 < 0.5 \cdot D \cdot \theta < 0.56 \tag{2}$$

wherein f designates the combined focal length of the positive first lens element and the positive second lens element (the focal length of the entire endoscope illumination optical system);

D designates the maximum diameter of the surface light source;

R1 designates the radius of curvature of a first surface, of the positive first lens element, facing toward the surface light source;

R2 designates the radius of curvature of a second surface, of the positive first lens element, facing toward a surface to be illuminated;

n1 designates the refractive index of the positive first lens element;

d1 designates the thickness of the positive first lens element; and

θ designates an angle defined as $(1+0.85d1/R2)(1-1/n1)/R1 - 1.05/R2$.

The endoscope illumination optical system further satisfies the following condition:

$$0.65 < d1/f < 1.0 \tag{3}$$

wherein d1 designates the thickness of the positive first lens element; and f designates the combined focal length of the positive first lens element and the positive second lens element (the focal length of the entire endoscope illumination optical system);

The endoscope illumination optical system preferably satisfies the following condition:

$$1.5 < (d0+H1)/f < 3.5 \tag{4}$$

wherein d0 designates the equivalent air thickness from the surface light source to the positive first lens element;

H1 designates the distance from the surface of the positive first lens element facing toward the surface light source to the principal point of the entire the endoscope illumination optical system on the side of the surface light source; and f designates the combined focal length of the positive first lens element and the positive second lens element (the focal length of the entire endoscope illumination optical system).

The endoscope illumination optical system according to the present invention is preferably provided with a cylindrical reflection body which has an inner cylindrical reflection surface about the optical axis. The cylindrical reflection body is positioned between the surface light source and the positive first lens element.

The cylindrical reflection body is preferably formed as a hollow tubular body having a mirror surface on the inner surface thereof, or, formed as a single rod having a core portion and a peripheral cylindrical cladding portion.

Instead of the cylindrical reflection body, the positive first lens element itself is formed as a single rod lens element having an reflection surface on the inner peripheral surface thereof (an inner reflection surface) about the optical axis, and the single rod lens element preferably satisfies the following condition:

$$2.0 < d1/(n1 \cdot f) < 3.5 \tag{5}$$

wherein d1 designates the thickness of the single rod lens element;

n1 designates the refractive index of the single rod lens element; and f designates the combined focal length of the positive first lens element and the positive second lens element (the focal length of the entire endoscope illumination optical system);

Furthermore, the single rod lens element is constituted by a core portion and a peripheral cylindrical cladding portion.

An LED or an exit surface of a light guide bundle can practically be used as the surface light source.

The endoscope illumination optical system preferably satisfies the following condition:

$$-5 < R4/D < -3.2 \tag{6}$$

wherein

R4 designates the radius of curvature of a surface of the positive second lens element facing toward a surface to be illuminated; and D designates the maximum diameter of the surface light source.

The present disclosure relates to subject matter contained in Japanese Patent Application No. 2006-229645 (filed on Aug. 25, 2006) which is expressly incorporated herein in its entirety.

BRIEF DESCRIPTION OF THE DRAWINGS

The present invention will be discussed below in detail with reference to the accompanying drawings, in which.

DESCRIPTION OF THE PREFERRED EMBODIMENTS

Figure 1:
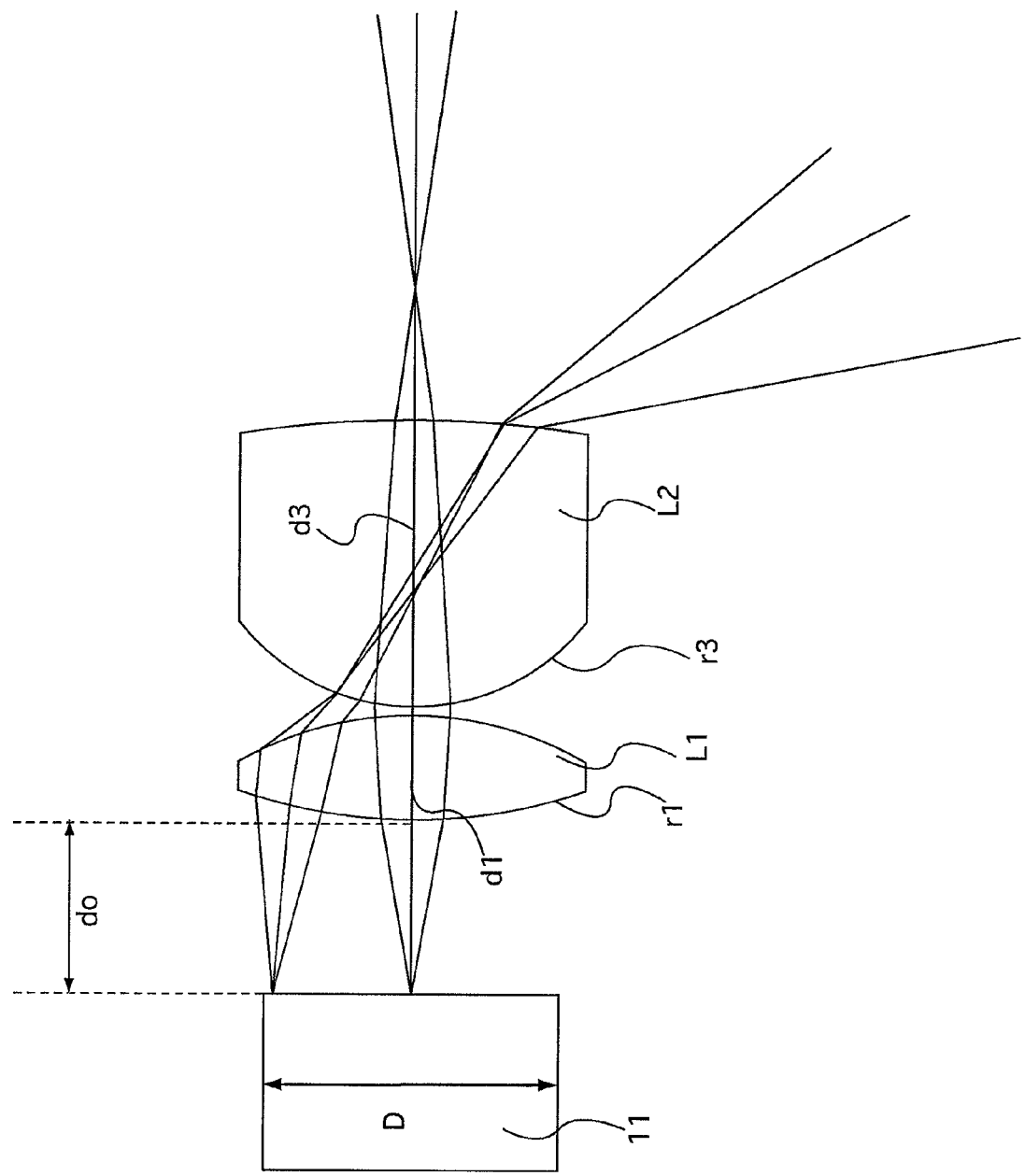
FIG. 1 is a lens arrangement of the endoscope illumination optical system according to a first embodiment of the present invention.

FIG. 1 is the lens arrangement of the endoscope illumination optical system according to the first embodiment. The endoscope illumination optical system includes a surface light source 11, a positive first lens element L1 and a positive second lens element L2, in this order from the surface light source 11; and a space (a distance d0) is provided between the surface light source 11 and the positive first lens element L1.

Figure 2:
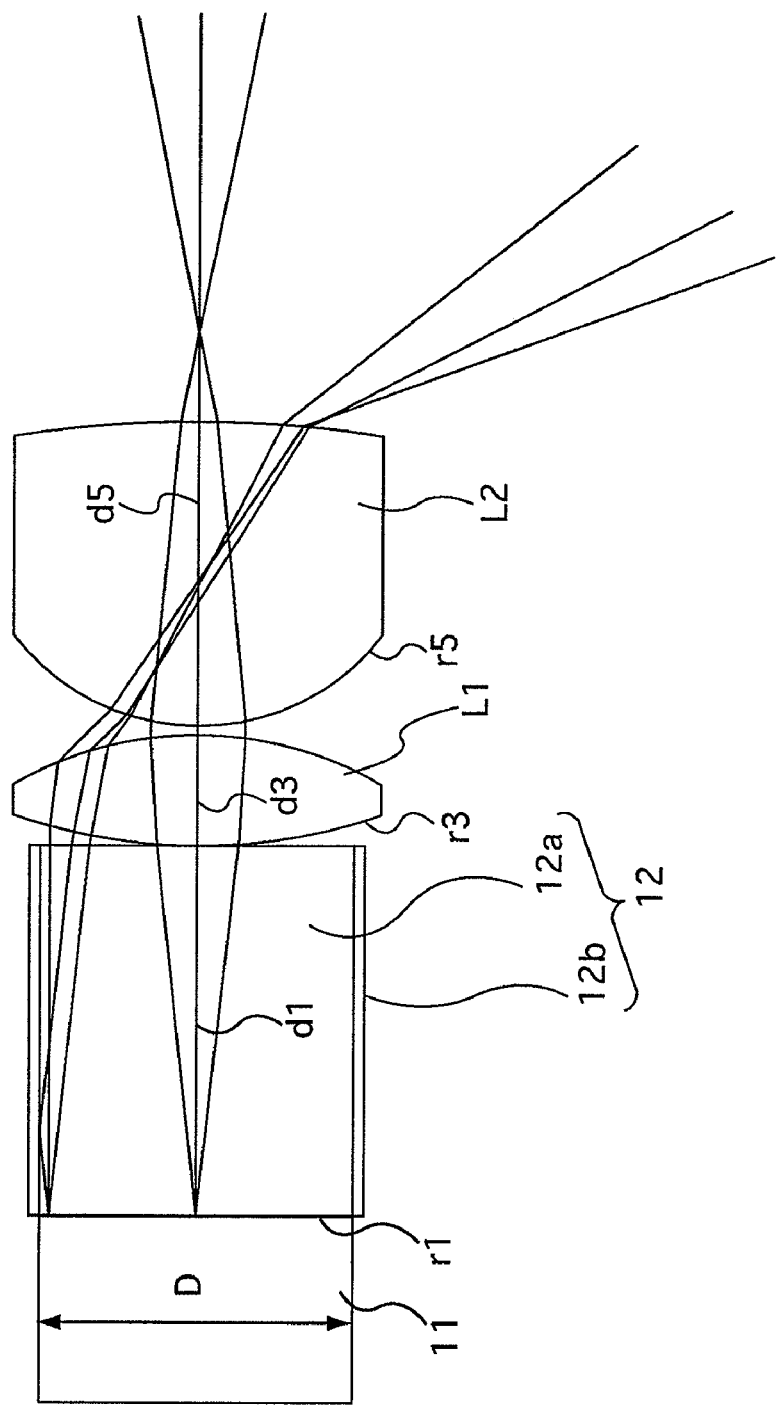
FIG. 2 is a common lens arrangement of the endoscope illumination optical system according to a second embodiment, a fourth embodiment, a fifth embodiment and a sixth embodiment of the present invention.

FIG. 2 is the common lens arrangement of the endoscope illumination optical system according to the second embodiment, the fourth embodiment, the fifth embodiment and the sixth embodiment. As a cylindrical reflection body which has an inner reflection surface about the optical axis, a single rod 12 constituted by a core portion 12a and a peripheral cylindrical cladding portion 12b is provided between the surface light source 11 and the positive first lens element L1. The refractive index n1 of the core portion 12a is higher than the refractive index n2 of the peripheral cylindrical cladding portion 12b (n1>n2). The boundary surface between the central core portion 12a and the peripheral cylindrical cladding portion 12b constitutes a reflection surface.

Figure 3:
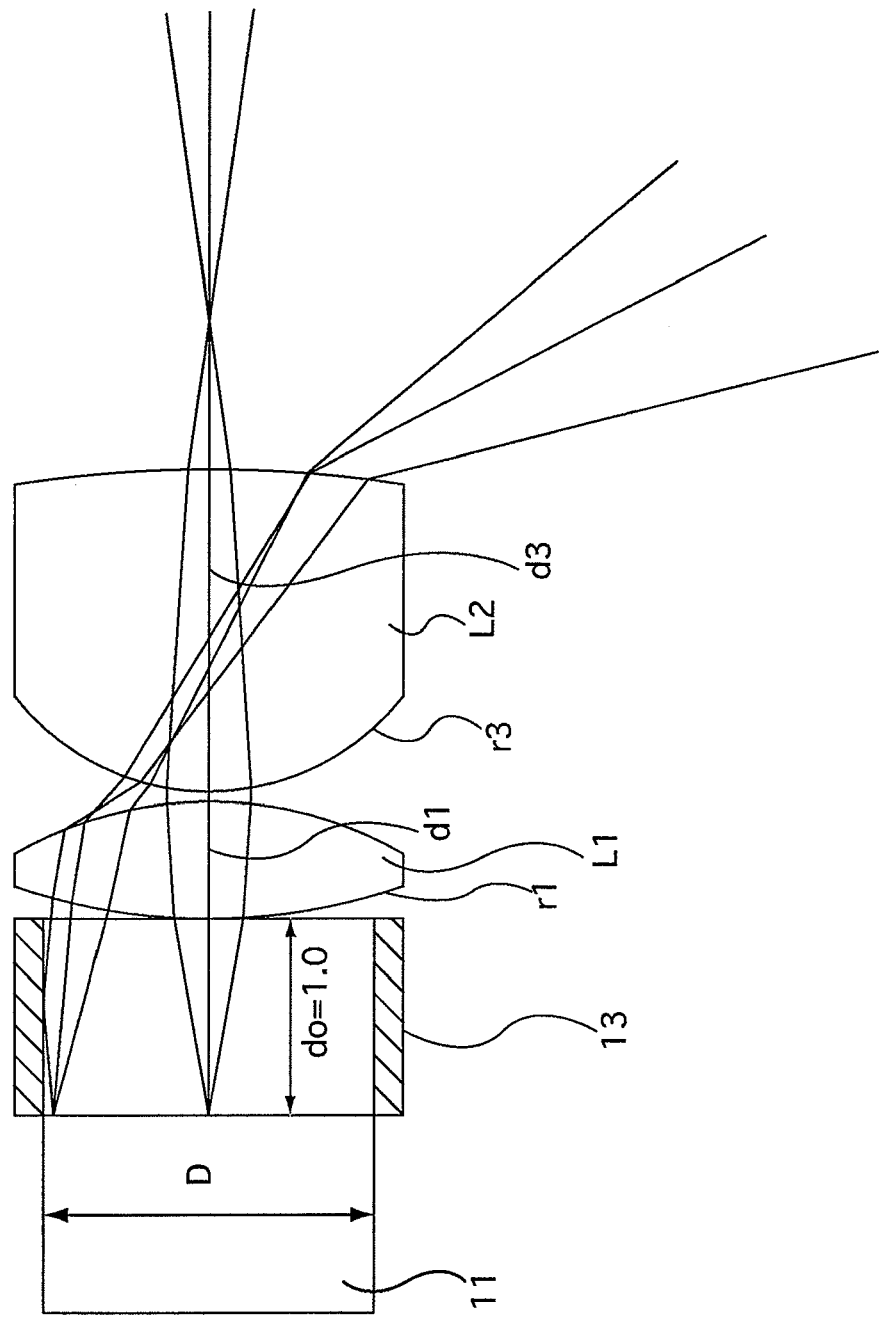
FIG. 3 is a lens arrangement of the endoscope illumination optical system according to a third embodiment of the present invention.

FIG. 3 is the lens arrangement of the endoscope illumination optical system according to the third embodiment. As a cylindrical reflection body which has an inner reflection surface about the optical axis, a hollow cylindrical body 13 in which the inner surface thereof is formed as a mirror surface is provided between the surface light source 11 and the positive first lens element L1.

Figure 4:
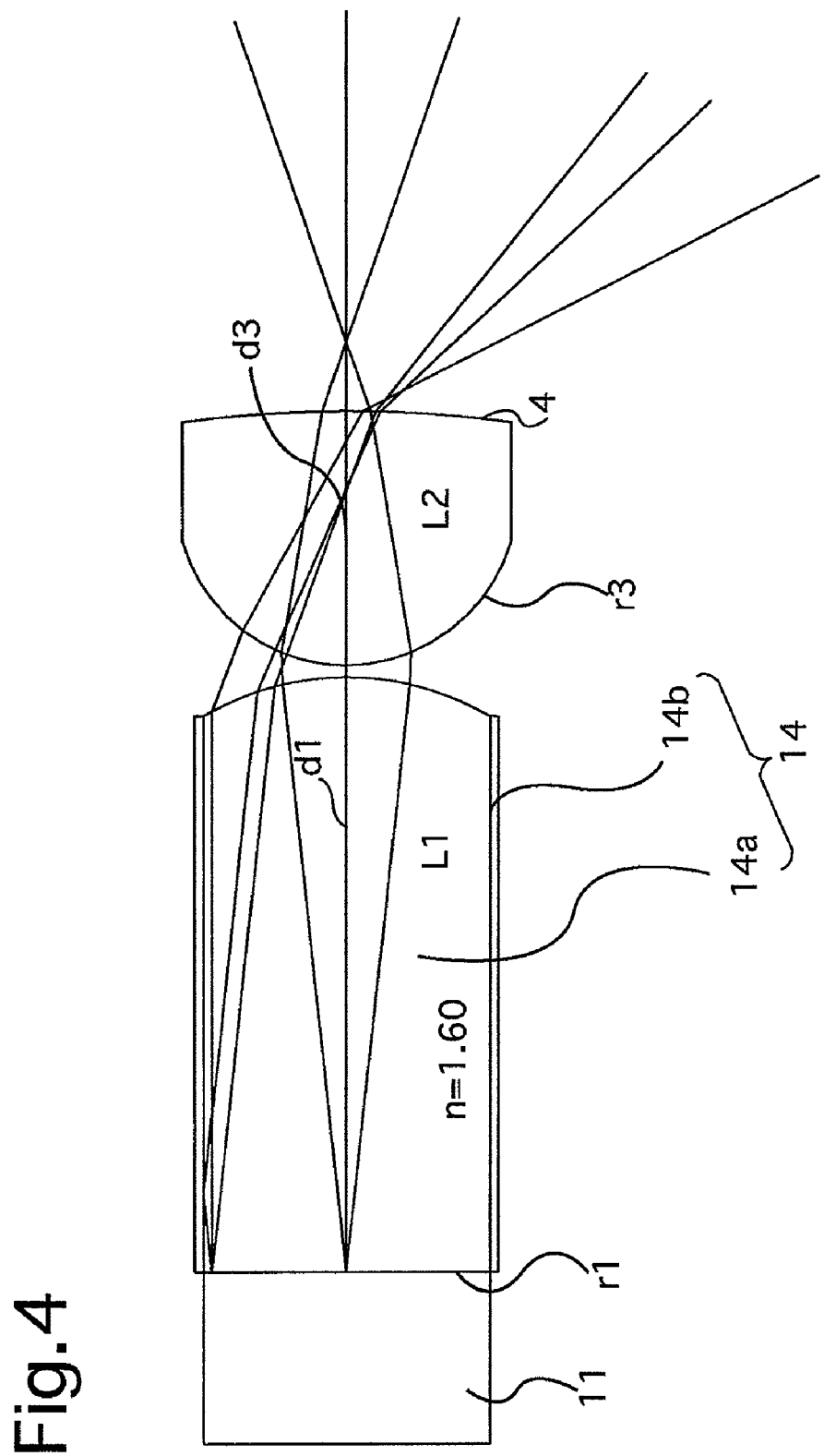
FIG. 4 is a common lens arrangement of the endoscope illumination optical system according to a seventh embodiment, an eighth embodiment and a ninth embodiment of the present invention.

FIG. 4 is the common lens arrangement of the endoscope illumination optical system according to the seventh embodiment, the eighth embodiment and the ninth embodiment. As a cylindrical reflection body which has an inner reflection surface about the optical axis, the positive first lens element L1 itself is formed as a single rod lens element having a central core portion 14a and the peripheral cylindrical cladding portion 14b. The refractive index n1 of the central core portion 14a is higher than the refractive index n2 of the peripheral cylindrical cladding portion 14b (n1>n2). The boundary surface between the central core portion 14a and the peripheral cylindrical cladding portion 14b constitutes a reflection surface.

Condition (1) specifies the ratio of the combined focal length of positive first lens element L1 and the positive second lens element L2 (the focal length of the entire endoscope illumination optical system) to the diameter of the surface light source 11.

If f/D exceeds the lower limit of condition (1), the combined focal length of positive first lens element L1 and the positive second lens element L2 becomes shorter. Consequently, the radius of curvature of each lens surface becomes smaller, so that the amount of light-quantity loss becomes larger.

If f/D exceeds the upper limit of condition (1), it becomes difficult to obtain a larger light distribution angle.

Figure 5:
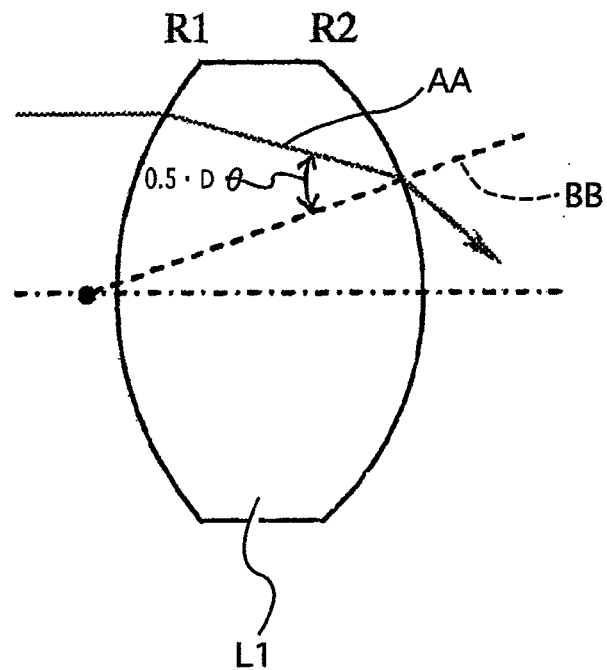
FIG. 5 is a side view of the positive first lens element for explaining condition (2)

Condition (2) includes an approximation formula (D·θ). The approximation formula is to define the angle 0.5·D·θ, as show in FIG. 5, formed by a light ray AA and a line BB which is a normal on the second surface of the positive first lens element L1, facing toward a surface to be illuminated.

Here, note that the unit of (D·θ) is radian (rad).

The light ray AA is emitted from the most peripheral edge of the surface light source 11, progresses parallel to the optical axis, is incident on the first surface of the positive first lens element L1, and incident on the second surface thereof.

The line BB is the normal at a point, on the second surface of the positive first lens element L1, where the light ray AA is incident.

If 0.5·D·θ exceeds the lower limit of condition (2), the amount of refraction on the second surface of the positive first lens element L1 is smaller, so that the angle of light distribution cannot be made larger.

If 0.5·D·θ exceeds the upper limit of condition (2), the number of light rays which are totally reflected on the second surface of the positive first lens element L1 increases, so that the amount of light-quantity loss becomes larger.

Condition (3) specifies the thickness of the positive first lens element L1.

If d1/f exceeds the lower limit of condition (3), the thickness of the positive first lens element L1 becomes thinner, so that it becomes difficult to secure a sufficient peripheral-edge thickness thereof.

If d1/f exceeds the upper limit of condition (3), the focal length of the positive first lens element L1 becomes longer, so that the light distribution angle becomes narrower.

Condition (4) is for preventing the mesh pattern of a light guide bundle from being viewed in the case where the surface light source 11 is constituted by an end-surface of the light guide bundle.

Namely, in an endoscope illumination optical system in which a light distribution lens element(s) is provided so that the entire light distribution lens element(s) has a positive refractive power, there is a case where an image of the light source (surface light source 11) is projected on a surface to be illuminated, depending on the positional relationship between the light source and the light distribution lens.

A light guide bundle which is widely used as a light source for an endoscope illumination optical system only emits light from the central core of each optical fiber; and light is not emitted from the peripheral cylindrical cladding portion nor from gaps among the optical fibers. Therefore a mesh pattern (formed by lighting portions and non-lighting portions) is projected onto a surface to be illuminated when the image of the light source is projected, which may cause an adverse influence in viewing.

Condition (4) specifies the positional relationship between the surface light source 11 and the positive first lens element L1 so that a position which is optically conjugate with the surface light source 11 is arranged not to be in the viewing area, so that the mesh pattern is not projected.

If (d0+H1)/f exceeds the lower limit of condition (4), a position which is optically conjugate with the surface light source 11 becomes farther from the light distribution lens elements (the positive first lens element L1 and the positive second lens element L2), and is in the depth-of-field of the objective lens element (not shown) of the endoscope. Consequently, there is an adverse influence in viewing.

If (d0+H1)/f exceeds the upper limit of condition (4), the overall length of the endoscope becomes longer, so that miniaturization thereof becomes difficult.

On the other hand, condition (4) is to determine that the distance between the surface light source 11 and the positive first lens element L1 should be longer than a predetermined distance. As a result of satisfying condition (4), a part of the diverging bundle of light rays from the surface light source 11 is not incident on the positive first lens element L1, so that light quantity loss occurs.

Then, in order to prevent such light quantity loss, it is preferable that the single rod 12 (FIG. 2) having the inner reflection surface about the optical axis, and a hollow cylindrical body 13 (FIG. 3) in which the inner surface thereof is formed as a mirror surface be provided between the surface light source 11 and the positive first lens element L1.

In connection with the single rod 12, in FIG. 4 (the seventh to ninth embodiments), the positive first lens element L1 is arranged to have the function of the single rod 12 as well, as a single rod lens element 14. According to this arrangement, unevenness of illumination can be prevented by a single optical element (i.e., the single rod lens element 14).

Condition (5) specifies the thickness of the positive first lens element L1 (the single rod lens element 14) in the case where the single rod lens element 14 has the reflection surface on the inner peripheral surface thereof.

If $d1/(n1 \cdot f)$ exceeds the lower limit of condition (5), a position which is optically conjugate with the surface light source 11 is in the depth-of-field of the objective lens element of the endoscope. Consequently, there is an adverse influence in viewing, specifically in the case where the surface light source 11 is constituted by an end-surface of the light guide bundle.

If $d1/(n1 \cdot f)$ exceeds the upper limit of condition (5), the overall length of the endoscope illumination optical system becomes longer, so that miniaturization cannot be achieved.

Due to the single rod lens element 14, a structure in which the reflection surface is formed on the inner peripheral surface of the positive first lens element L1 can easily attained.

The second surface (facing toward a surface to be illuminated) of the positive second lens element L2 is preferably arranged to have a larger radius of curvature R4 (FIG. 4).

Condition (6) specifies the range of the radius of curvature R4.

If R4/D exceeds the lower limit of condition (6), the difference in the refractive power between the light rays having a narrow light distribution angle and the light rays having a wide light distribution angle increases. Furthermore, light rays which are bent by more than a predetermined angle are totally reflected, so that the amount of peripheral illumination becomes insufficient.

If R4/D exceeds the upper limit of condition (6), the refractive power of the light rays emitted from the most peripheral edge of the surface light source 11 becomes weaker, so that the light distribution angle becomes smaller.

Furthermore, since the radius of curvature R4 becomes smaller, the front of the second lens element L2 largely protrudes from the distal end of the endoscope, so that washing of the second lens element L2 becomes difficult; and the second lens element L2 is vulnerable to being scratched (damaged).

Specific numerical data of the embodiments will be described hereinafter.

In the tables, f designates the focal length of the entire lens system, r designates the radius of curvature, d designates the lens-element thickness or a distance between lens elements, $N_d$ designates the refractive index of the d-line, and ν designates the Abbe number.

In FIGS. 7 to 14 (the diagrams of the light-distribution characteristics), the horizontal axis designates the angle of a light ray with respect to the optical axis (Angle [deg]), and the vertical axis (a.u. (arbitrary unit)) designates the relative intensity which is obtained by defining the intensity at the central portion of the endoscope illumination optical system (i.e., on the optical axis) as 1.

Embodiment 1

FIG. 1 is the lens arrangement of the endoscope illumination optical system according to the first embodiment.

Figure 7:
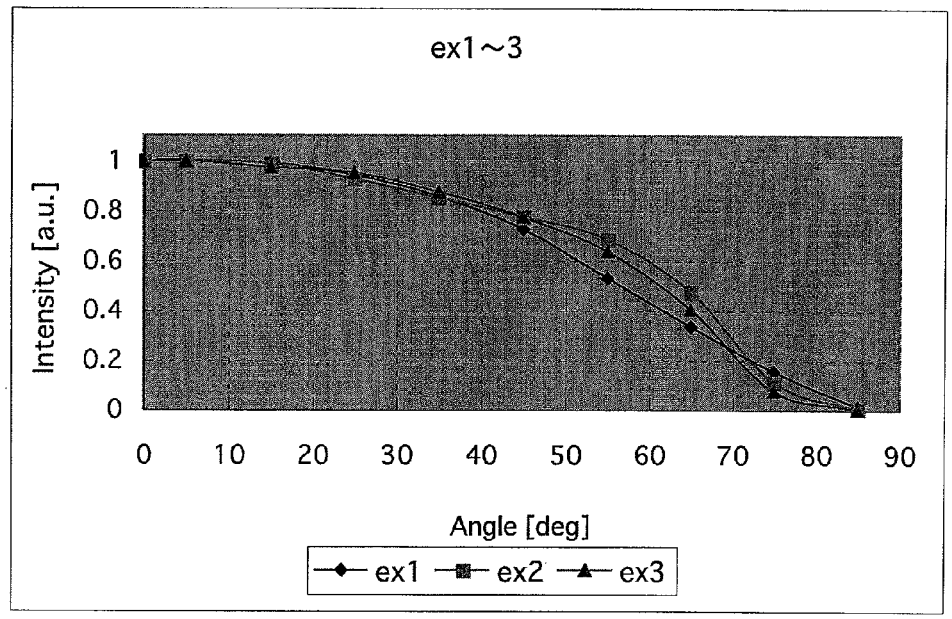
FIG. 7 is a diagram of light-distribution characteristics of the endoscope illumination optical system according to the first to third embodiments of the present invention.

FIG. 7 is the diagram of light-distribution characteristics of the endoscope illumination optical system according to the first to third embodiments.

Table 1 shows numerical date of the first embodiment.

The maximum diameter D of the surface light source 11 is φ=1.7.

TABLE 1 f = 0.79
d0 = 1.00

| Surf. No. | r | d | Nd | ν |
|---|---|---|---|---|
| 1 | 3.093 | 0.60 | 1.88300 | 40.8 |
| 2 | −2.000 | 0.05 | | |
| 3 | 1.266 | 1.65 | 1.88300 | 40.8 |
| 4 | −6.375 | — | | |

Embodiment 2

FIG. 2 is the common lens arrangement of the endoscope illumination optical system according to the second embodiment, the fourth embodiment, the fifth embodiment and the sixth embodiment.

FIG. 7 is the diagram of light-distribution characteristics of the endoscope illumination optical system according to the first to third embodiments.

Table 2 shows numerical date of the second embodiment.

Surface Nos. 1 and 2 are the incident and exit surfaces of the single rod 12.

The maximum diameter D of the surface light source 11 equals the diameter of the central core portion 12a of the single rod 12, i.e., ϕ=1.7.

The refractive index n1 of the central core portion 12a is 1.60.

The refractive index n2 of peripheral cylindrical cladding portion 12b is 1.51.

TABLE 2 f = 0.79
d0 = d1/n1 + d2 = 2.00/1.60000 + 0.00 = 1.25

| Surf. No. | r | d | Nd | ν |
|---|---|---|---|---|
| 1 | ∞ | 2.00 | 1.60000 | 55.0 |
| 2 | ∞ | 0.00 | | |
| 3 | 3.093 | 0.60 | 1.88300 | 40.8 |
| 4 | −2.000 | 0.05 | | |
| 5 | 1.266 | 1.65 | 1.88300 | 40.8 |
| 6 | −6.375 | — | | |

Embodiment 3

FIG. 3 is the lens arrangement of the endoscope illumination optical system according to the third embodiment.

FIG. 7 is the diagram of light-distribution characteristics of the endoscope illumination optical system according to the first to third embodiments.

Table 3 shows numerical date of the third embodiment.

The basic lens arrangement of the third embodiment is the same as that of the first embodiment; however, the hollow cylindrical body 13 in which the inner surface thereof is formed as a mirror surface is provided between the surface light source 11 and the positive first lens element L1.

The maximum diameter D of the surface light source 11 equals the inner diameter of the hollow cylindrical body 13, i.e., ϕ=1.7.

The reflection ratio of the inner diameter of the hollow cylindrical body 13 is 65%.

TABLE 3 f = 0.79
d0 = 1.00

| Surf. No. | r | d | Nd | ν |
|---|---|---|---|---|
| 1 | 3.093 | 0.60 | 1.88300 | 40.8 |
| 2 | −2.000 | 0.05 | | |
| 3 | 1.266 | 1.65 | 1.88300 | 40.8 |
| 4 | −6.375 | — | | |

Embodiment 4

FIG. 2 is the common lens arrangement of the endoscope illumination optical system according to the second embodiment, the fourth embodiment, the fifth embodiment and the sixth embodiment.

Figure 8:
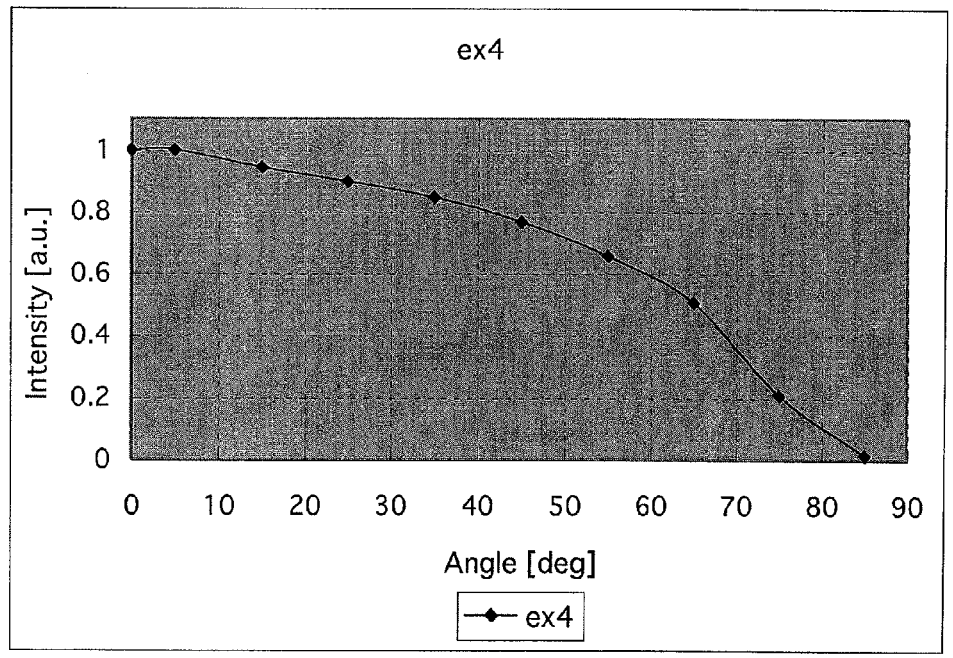
FIG. 8 is a diagram of a light-distribution characteristic of the endoscope illumination optical system according to the fourth embodiment of the present invention.

FIG. 8 is the diagram of a light-distribution characteristic of the endoscope illumination optical system according to the fourth embodiment.

Table 4 shows numerical date of the fourth embodiment.

Surface Nos. 1 and 2 are the incident and exit surfaces of the single rod 12.

The maximum diameter D of the surface light source 11 equals the diameter of the central core portion 12a of the single rod 12, i.e., ϕ=1.7.

The refractive index n1 of the central core portion 12a is 1.60.

The refractive index n2 of peripheral cylindrical cladding portion 12b is 1.51.

TABLE 4 f = 0.81
d0 = d1/n1 + d2 = 2.40/1.60000 + 0.03 = 1.53

| Surf. No. | r | d | Nd | ν |
|---|---|---|---|---|
| 1 | ∞ | 2.40 | 1.60000 | 55.0 |
| 2 | ∞ | 0.03 | | |
| 3 | 2.314 | 0.76 | 1.88300 | 40.8 |
| 4 | −2.314 | 0.05 | | |
| 5 | 1.275 | 1.61 | 1.88300 | 40.8 |
| 6 | −7.083 | — | | |

Embodiment 5

FIG. 2 is the common lens arrangement of the endoscope illumination optical system according to the second embodiment, the fourth embodiment, the fifth embodiment and the sixth embodiment.

Figure 9:
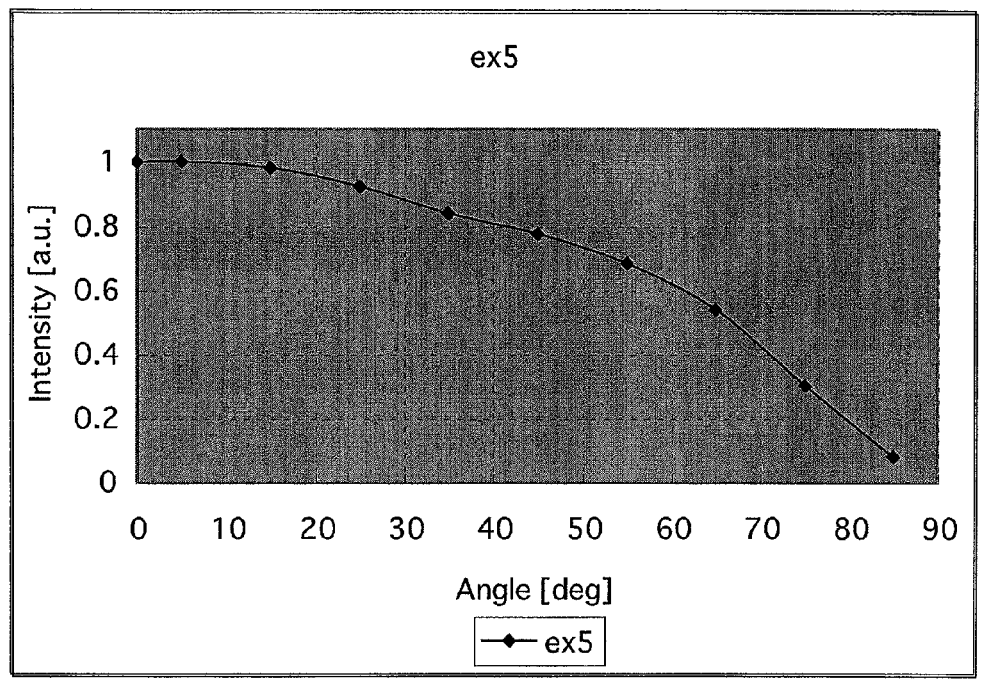
FIG. 9 is a diagram of a light-distribution characteristic of the endoscope illumination optical system according to the fifth embodiment of the present invention.

FIG. 9 is the diagram of a light-distribution characteristic of the endoscope illumination optical system according to the fifth embodiment.

Table 5 shows numerical date of the fifth embodiment.

Surface Nos. 1 and 2 are the incident and exit surfaces of the single rod 12.

The maximum diameter D of the surface light source 11 equals the diameter of the central core portion 12a of the single rod 12, i.e., ϕ=1.7.

The refractive index n1 of the central core portion 12a is 1.60.

The refractive index n2 of peripheral cylindrical cladding portion 12b is 1.51.

TABLE 5

| | f = 0.75 | | | |
|---|---|---|---|---|
| | d0 = d1/n1 + d2 = 2.20/1.60000 + 0.05 = 1.425 | | | |
| Surf. No. | r | d | Nd | ν |
| 1 | ∞ | 2.20 | 1.60000 | 55.0 |
| 2 | ∞ | 0.05 | | |
| 3 | 2.196 | 0.66 | 1.88300 | 40.8 |
| 4 | −2.196 | 0.05 | | |
| 5 | 1.157 | 1.46 | 1.88300 | 40.8 |
| 6 | −5.903 | — | | |

Embodiment 6

FIG. 2 is the common lens arrangement of the endoscope illumination optical system according to the second embodiment, the fourth embodiment, the fifth embodiment and the sixth embodiment.

Figure 10:
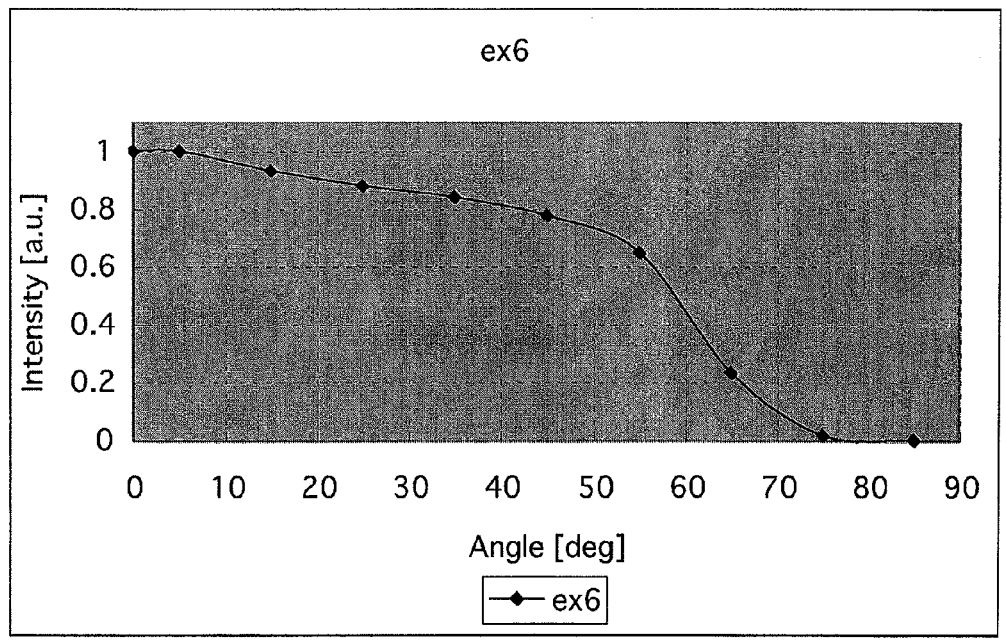
FIG. 10 is a diagram of a light-distribution characteristic of the endoscope illumination optical system according to the sixth embodiment of the present invention.

FIG. 10 is the diagram of a light-distribution characteristic of the endoscope illumination optical system according to the sixth embodiment.

Table 6 shows numerical date of the sixth embodiment.

Surface Nos. 1 and 2 are the incident and exit surfaces of the single rod 12.

The maximum diameter D of the surface light source 11 equals the diameter of the central core portion 12a of the single rod 12, i.e., φ=1.7.

The refractive index n1 of the central core portion 12a is 1.60.

The refractive index n2 of peripheral cylindrical cladding portion 12b is 1.51.

TABLE 6

| | f = 0.90 | | | |
|---|---|---|---|---|
| | d0 = d1/n1 + d2 = 2.20/1.60000 + 0.05 = 1.425 | | | |
| Surf. No. | r | d | Nd | ν |
| 1 | ∞ | 2.20 | 1.60000 | 55.0 |
| 2 | ∞ | 0.05 | | |
| 3 | 3.088 | 0.66 | 1.88300 | 40.8 |
| 4 | −2.408 | 0.10 | | |
| 5 | 1.417 | 1.70 | 1.88300 | 40.8 |
| 6 | −7.083 | — | | |

Embodiment 7

FIG. 4 is the common lens arrangement of the endoscope illumination optical system according to a seventh embodiment, an eighth embodiment and a ninth embodiment.

Figure 11:
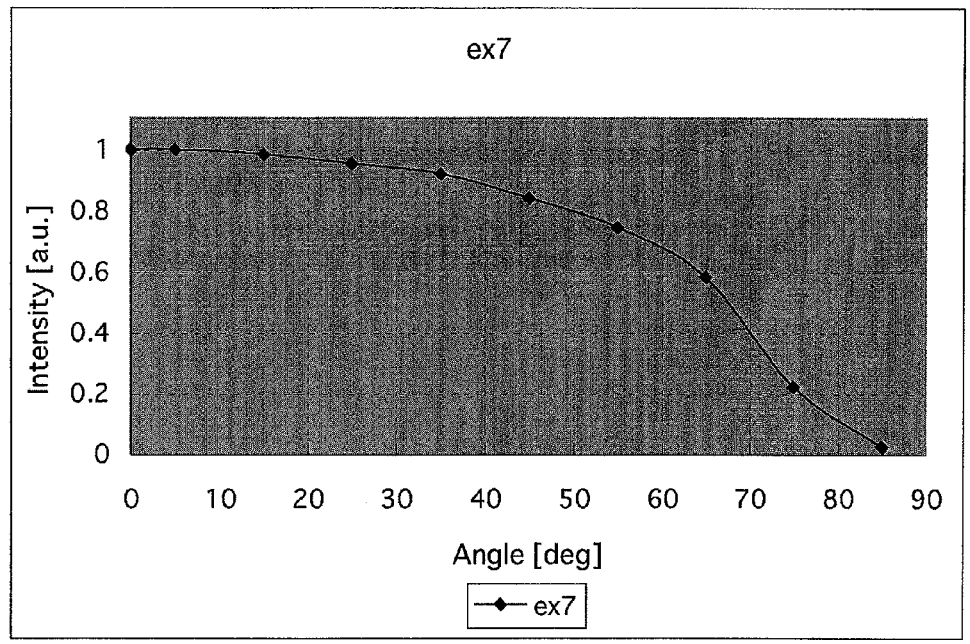
FIG. 11 is a diagram of a light-distribution characteristic of the endoscope illumination optical system according to the seventh embodiment of the present invention.

FIG. 11 is the diagram of a light-distribution characteristic of the endoscope illumination optical system according to the seventh embodiment.

Table 7 shows numerical date of the seventh embodiment.

Surface Nos. 1 and 2 are the incident and exit surfaces of the single rod lens element 14.

The maximum diameter D of the surface light source 11 equals the diameter of the central core portion 14a of the single rod lens element 14, i.e., φ=1.7.

The refractive index n1 of the central core portion 14a is 1.60.

The refractive index n2 of peripheral cylindrical cladding portion 14b is 1.51.

TABLE 7

| | f = 0.83 | | | |
|---|---|---|---|---|
| | d0 = 0.00 | | | |
| Surf. No. | r | d | Nd | ν |
| 1 | ∞ | 3.50 | 1.60000 | 55.0 |
| 2 | −1.676 | 0.07 | | |
| 3 | 1.015 | 1.50 | 1.88300 | 40.8 |
| 4 | −7.083 | — | | |

Embodiment 8

FIG. 4 is the common lens arrangement of the endoscope illumination optical system according to a seventh embodiment, an eighth embodiment and a ninth embodiment.

Figure 12:
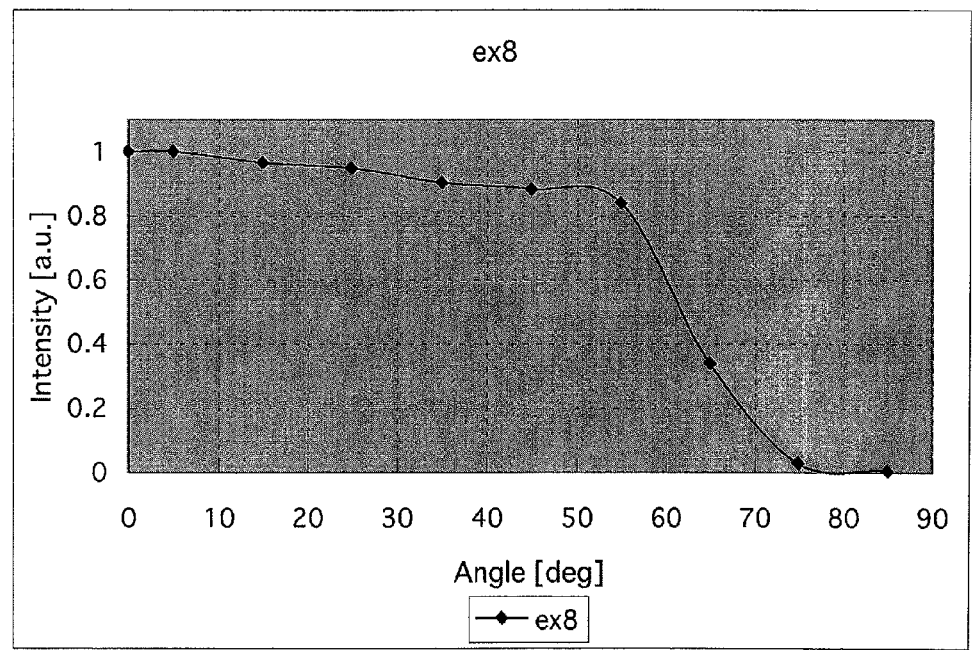
FIG. 12 is a diagram of a light-distribution characteristic of the endoscope illumination optical system according to the eighth embodiment of the present invention.

FIG. 12 is the diagram of a light-distribution characteristic of the endoscope illumination optical system according to the eighth embodiment.

Table 8 shows numerical date of the eighth embodiment.

Surface Nos. 1 and 2 are the incident and exit surfaces of the single rod lens element 14.

The maximum diameter D of the surface light source 11 equals the diameter of the central core portion 14a of the single rod lens element 14, i.e., φ=1.7.

The refractive index n1 of the central core portion 14a is 1.60.

The refractive index n2 of peripheral cylindrical cladding portion 14b is 1.51.

TABLE 8

| | f = 0.86 | | | |
|---|---|---|---|---|
| | d0 = 0.00 | | | |
| Surf. No. | r | d | Nd | ν |
| 1 | ∞ | 2.95 | 1.60000 | 55.0 |
| 2 | −1.690 | 0.23 | | |
| 3 | 1.015 | 1.46 | 1.88300 | 40.8 |
| 4 | −7.083 | — | | |

Embodiment 9

FIG. 4 is the common lens arrangement of the endoscope illumination optical system according to a seventh embodiment, an eighth embodiment and a ninth embodiment.

Figure 13:
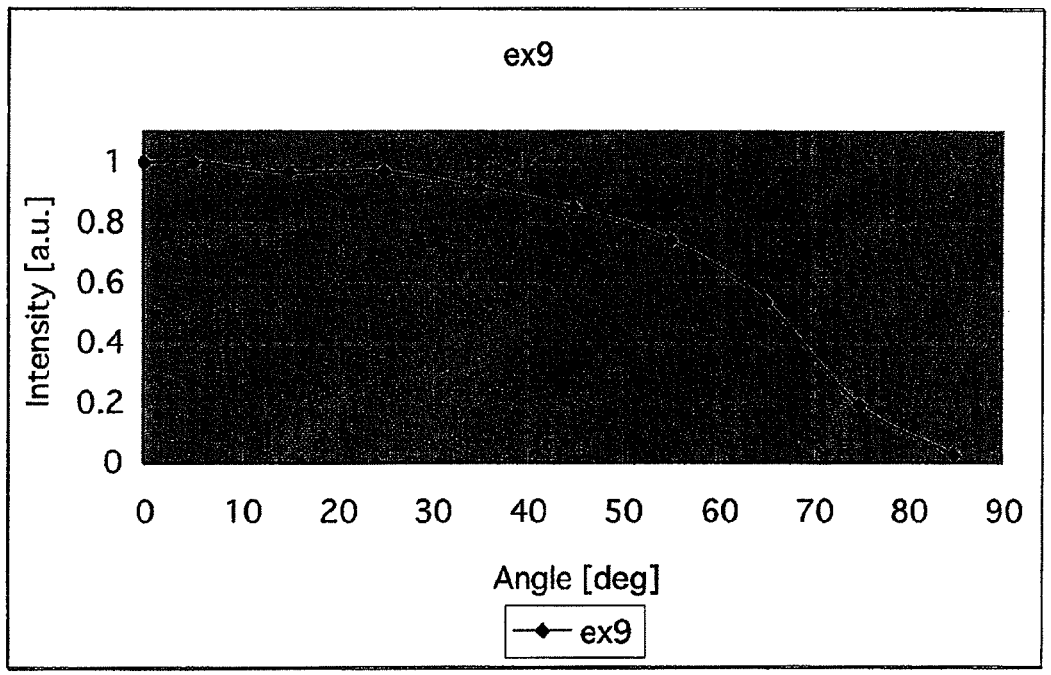
FIG. 13 is a diagram of a light-distribution characteristic of the endoscope illumination optical system according to the ninth embodiment of the present invention.

FIG. 13 is the diagram of a light-distribution characteristic of the endoscope illumination optical system according to the ninth embodiment.

Table 9 shows numerical date of the ninth embodiment.

Surface Nos. 1 and 2 are the incident and exit surfaces of the single rod lens element 14.

The maximum diameter D of the surface light source 11 equals the diameter of the central core portion 14a of the single rod lens element 14, i.e., φ=1.7.

The refractive index n1 of the central core portion 14a is 1.60.

The refractive index n2 of peripheral cylindrical cladding portion 14b is 1.51.

TABLE 9 f = 0.85
d0 = 0.00

| Surf. No. | r | d | Nd | ν |
|---|---|---|---|---|
| 1 | ∞ | 3.78 | 1.60000 | 55.0 |
| 2 | −1.724 | 0.08 | | |
| 3 | 1.039 | 1.49 | 1.88300 | 40.8 |
| 4 | −8.028 | — | | |

COMPARATIVE EXAMPLE

Figure 6:
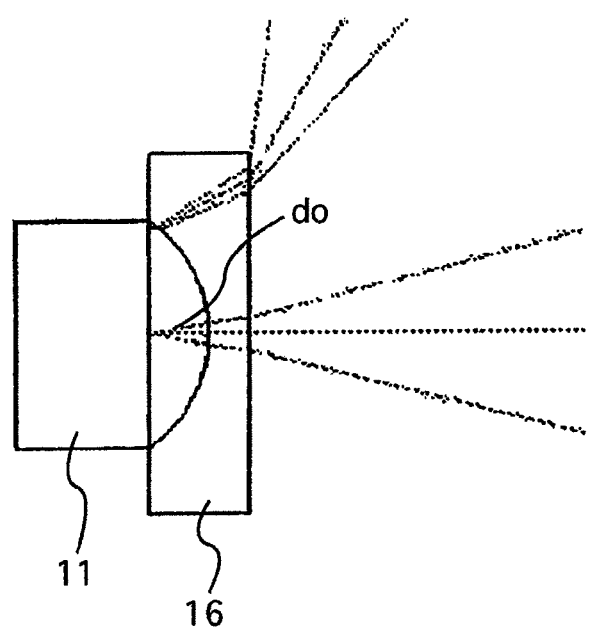
FIG. 6 shows a lens arrangement of an endoscope illumination optical system as a comparative example.

FIG. 6 shows the lens arrangement of an endoscope illumination optical system as a comparative example. More specifically, the endoscope illumination optical system as a comparative example include the surface light source 11 and a planoconcave lens element 16.

Figure 14:
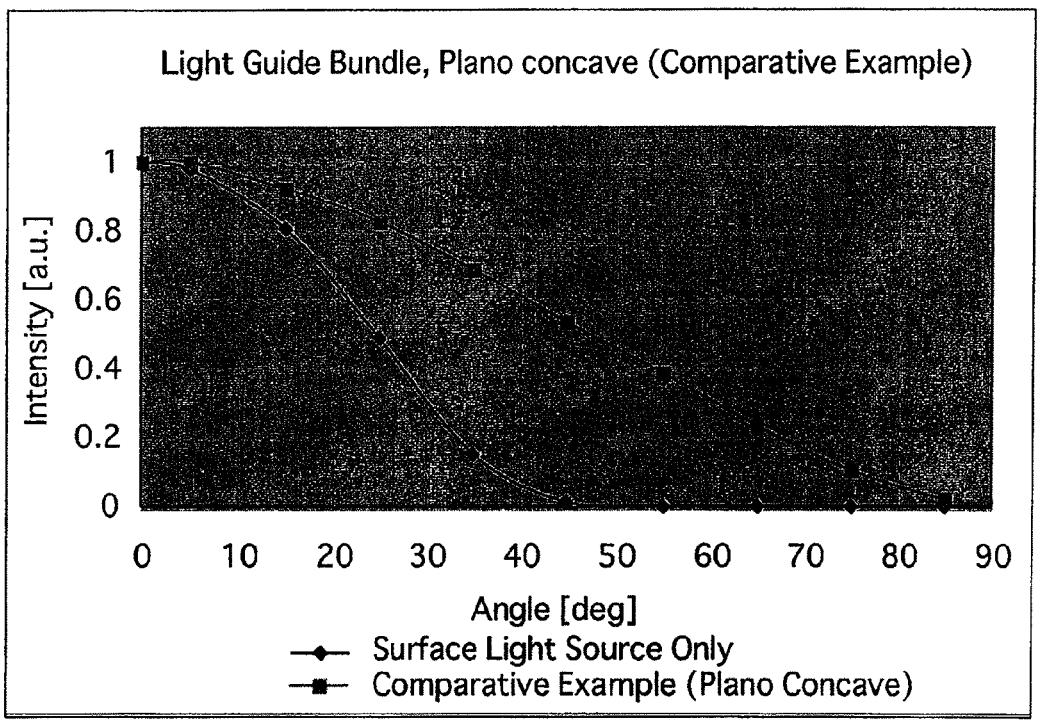
FIG. 14 is a diagram of a light-distribution characteristic of an endoscope illumination optical system as a comparative example.

FIG. 14 is the diagram of a light-distribution characteristic of an endoscope illumination optical system as the comparative example. Furthermore, FIG. 14 depicts a light-distribution characteristic of the surface light source 11 (the exit surface of a light guide bundle).

TABLE 10 f = −1.15
d0 = 0.46

| Surf. No. | r | d | Nd | ν |
|---|---|---|---|---|
| 1 | −1.015 | 0.30 | 1.88300 | 40.8 |
| 2 | ∞ | — | | |

The numerical values of each condition for each embodiment are shown in Table 11.

TABLE 11

| | Embod. 1 | Embod. 2 | Embod. 3 | Embod. 4 | Embod. 5 |
|---|---|---|---|---|---|
| Cond. (1) | 0.467 | 0.467 | 0.467 | 0.477 | 0.440 |
| Cond. (2) | 0.542 | 0.542 | 0.542 | 0.510 | 0.542 |
| Cond. (3) | 0.756 | 0.756 | 0.756 | 0.936 | 0.883 |
| Cond. (4) | 1.777 | 2.092 | 1.777 | 2.461 | 2.472 |
| Cond. (5) | 0.402 | 0.402 | 0.402 | 0.497 | 0.469 |
| Cond. (6) | −3.750 | −3.750 | −3.750 | −4.166 | −3.472 |

| | Embod. 6 | Embod. 7 | Embod. 8 | Embod. 9 |
|---|---|---|---|---|
| Cond. (1) | 0.528 | 0.487 | 0.508 | 0.499 |
| Cond. (2) | 0.470 | 0.533 | 0.528 | 0.518 |
| Cond. (3) | 0.736 | 4.228 | 3.413 | 4.456 |
| Cond. (4) | 2.111 | 2.805 | 2.439 | 2.943 |
| Cond. (5) | 0.391 | 2.642 | 2.133 | 2.785 |
| Cond. (6) | −4.166 | −4.166 | −4.166 | −4.772 |

As can be understood upon comparing each embodiment with the comparative example, the endoscope illumination optical system of the present invention has bright, superior light distribution at the periphery thereof.

Furthermore, as can be understood from Table 11, the first through ninth embodiments satisfy conditions (1), (2), (4) and (6).

The first through sixth embodiments satisfy condition (3).

The seventh through ninth embodiments do not satisfy condition (3). This is because the positive first lens element L1 itself is formed as the single rod lens element 14.

On the other hand, the seventh through ninth embodiments employing the single rod lens element 14 satisfy condition (5).

According to the above descriptions, an endoscope illumination optical system with two positive lens elements, which has the following features, can be attained:
(i) a superior light-distribution characteristic by which the periphery of an area to be illuminated is suitably illuminated;
(ii) a high light-utilization efficiency; and
(iii) low production costs.

Obvious changes may be made in the specific embodiments of the present invention described herein, such modifications being within the spirit and scope of the invention claimed. It is indicated that all matter contained herein is illustrative and does not limit the scope of the present invention.

What is claimed is:

1. An endoscope illumination optical system comprising:
a surface light source, a positive first lens element, and a positive second lens element, in this order from said surface light source,
wherein said endoscope illumination optical system satisfies the following conditions:

$$0.40 < f/D < 0.53$$

$$0.40 < 0.5 \cdot D \cdot \theta < 0.56$$

wherein:
f designates a combined focal length of said positive first lens element and said positive second lens element,
D designates a maximum diameter of said surface light source,
R1 designates a radius of curvature of a first surface of said positive first lens element facing toward said surface light source,
R2 designates a radius of curvature of a second surface of said positive first lens element facing toward a surface to be illuminated,
n1 designates a refractive index of said positive first lens element,
d1 designates a thickness of said positive first lens element, and
θ designates an angle defined as $(1+0.85d1/R2)(1-1/n1)/R1 - 1.05/R2$.

2. The endoscope illumination optical system according to claim 1, further satisfies the following condition:

$$0.65 < d1/f < 1.0$$

wherein:
d1 designates the thickness of said positive first lens element, and
f designates the combined focal length of said positive first lens element and said positive second lens element.

3. The endoscope illumination optical system according to claim 1, further satisfies the following condition:

$$1.5 < (d0+H1)/f < 3.5$$

wherein:
d0 designates an equivalent air thickness from said surface light source to said positive first lens element, and
H1 designates a distance from the first surface of said positive first lens element facing toward said surface light source to a principal point of the entire endoscope illumination optical system on a side of said surface light source.

4. The endoscope illumination optical system according to claim 1, further comprising:
   a cylindrical reflection body which has an inner cylindrical reflection surface about an optical axis of the endoscope illumination optical system,
   wherein said cylindrical reflection body is positioned between said surface light source and said positive first lens element.

5. The endoscope illumination optical system according to claim 4, wherein said cylindrical reflection body comprises a hollow tubular body.

6. The endoscope illumination optical system according to claim 4, wherein said cylindrical reflection body comprises a single rod comprising a core portion and a peripheral cylindrical cladding portion.

7. The endoscope illumination optical system according to claim 1, wherein said positive first lens element comprises a single rod lens element having an inner reflection surface about an optical axis of the endoscope illumination optical system, and
   wherein said single rod lens element satisfies the following condition:

$$2.0 < d1/(n1 \cdot f) < 3.5$$

wherein:
   d1 designates a thickness of said single rod lens element,
   n1 designates a refractive index of said single rod lens element, and
   f designates a combined focal length of said single rod lens element and said positive second lens element.

8. The endoscope illumination optical system according to claim 7, wherein said single rod lens element comprises a core portion and a peripheral cylindrical cladding portion.

9. The endoscope illumination optical system according to claim 1, wherein said surface light source comprises one of an LED and an exit surface of a light guide bundle.

10. The endoscope illumination optical system according to claim 1, further satisfies the following condition:

$$-5 < R4/D < -3.2$$

wherein:
   R4 designates a radius of curvature of a surface of said positive second lens element facing the surface to be illuminated, and
   D designates the maximum diameter of said surface light source.

\* \* \* \* \*